(12) United States Patent
Danger et al.

(10) Patent No.: US 6,261,096 B1
(45) Date of Patent: Jul. 17, 2001

(54) DENTAL TOOL HAVING TRIPLE TOOTHING

(75) Inventors: Karl-Heinz Danger, Detmold; Jürgen Schön, Kalletal, both of (DE)

(73) Assignee: Gebruder Brasseler GmbH & Co. KG, Lemgo (DE)

( * ) Notice: Subject to any disclaimer, the term of this patent is extended or adjusted under 35 U.S.C. 154(b) by 0 days.

(21) Appl. No.: 09/484,936

(22) Filed: Jan. 18, 2000

(30) Foreign Application Priority Data

Jan. 19, 1999 (DE) .............................. 199 01 929

(51) Int. Cl.⁷ .................................................. A61C 3/02
(52) U.S. Cl. .................................................. 433/165
(58) Field of Search ..................... 433/165, 166

(56) References Cited

U.S. PATENT DOCUMENTS 1,358,432 * 11/1920 Fink ..................................... 433/165
3,832,779 * 9/1974 Reynaud ............................... 433/165
4,284,406 * 8/1981 Hughes ................................ 433/165

FOREIGN PATENT DOCUMENTS

| 198 10 284 A1 | 9/1999 | (DE) | ................. A61C/3/06 |
| 0 493 701 A2 | 7/1992 | (EP) | ................. A61C/3/02 |

* cited by examiner

*Primary Examiner*—Nicholas D. Lucchesi
(74) *Attorney, Agent, or Firm*—Wolf, Greenfield & Sacks, P.C.

(57) ABSTRACT

The present invention relates to a dental tool (1) comprising a head (2) and a rotatably supported shaft (9). The head (2) comprises a first toothing (A), a second toothing (B), and a third toothing (C). Thus, different materials can be roughed and also finished by means of said triple toothing.

15 Claims, 2 Drawing Sheets

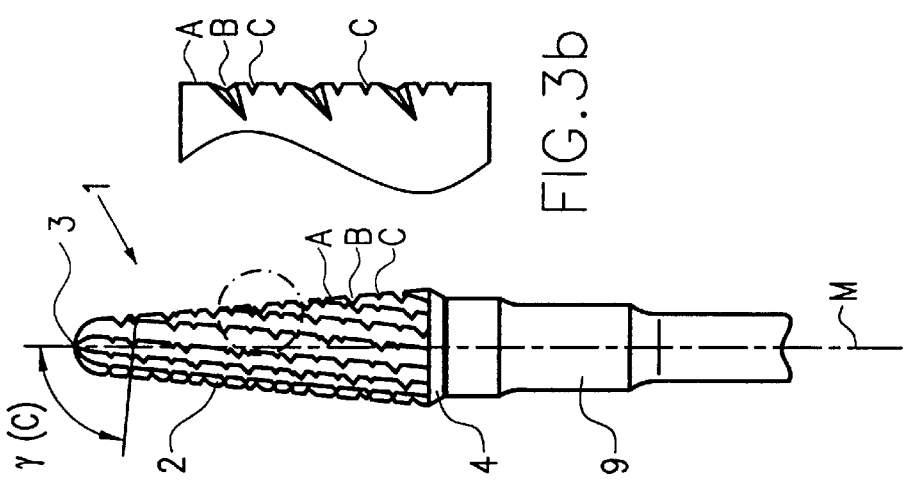
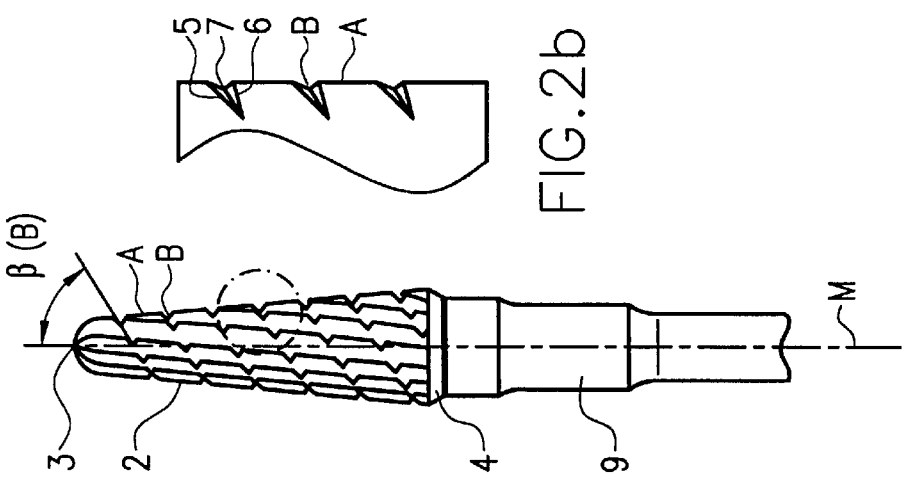
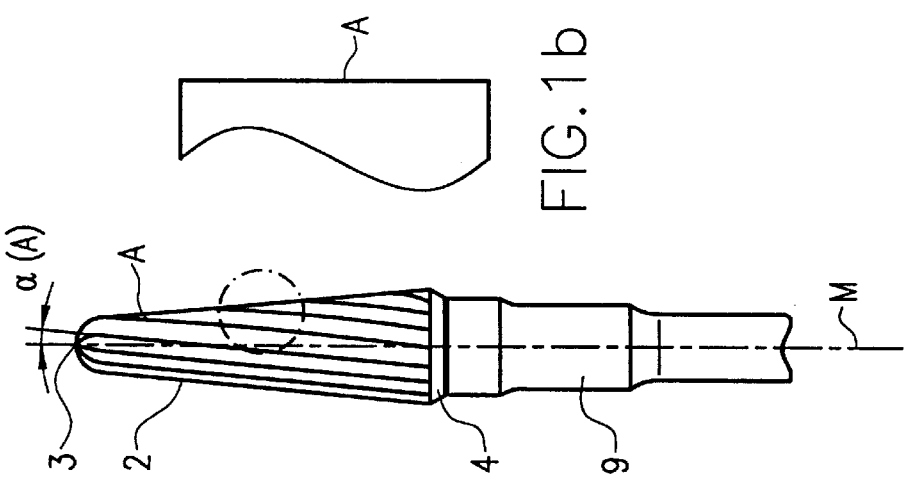

DENTAL TOOL HAVING TRIPLE TOOTHING

BACKGROUND

1. Field of the Invention

The present invention relates to an improved dental tool comprising a head and a shaft which can rotatably be supported in a drive device.

2. Related Art

In dental laboratories dental technicians are nowadays using, in particular, milling tools for machining the most different materials, said tools being preferably made from carbide. The surfaces, for example, of crowns, bridges, or the like, are machined with the help of said milling tools to subsequently finish and polish the surfaces with the help of high-precision grinding tools in an additional working step. The dental technician is here using different tools in successive order, which requires several tool-changing operations.

Hence, during machining, a dental technician has to provide different tools on the one hand, and the machining time is prolonged by several tool-changing operations on the other hand.

SUMMARY OF THE INVENTION

Therefore, it is the object of the present invention to provide a dental tool which can easily be handled and produced and is able to carry out different machining steps.

Said object is achieved by a dental tool comprising the features of claim 1. Advantageous developments are the subject matter of the subclaims.

Hence, a dental tool according to the invention comprises a first, second and third toothing. Thanks to such a triple toothing the dental tool according to the invention, in particular a dental milling cutter, is suited for both roughing and smoothing, which will hereinafter be referred to as finishing in accordance with technical dental language. Thus the triple toothing creates a universal tool which avoids troublesome tool-changing operations. The machining time can thereby be reduced considerably. The three toothings can each be used for different working steps.

Depending on the respective material, a dental technician can also vary the cutting characteristics of the dental tool with the triple toothing by selecting different speeds. A high speed is preferably chosen for roughing operations whereas a low speed is chosen for finishing work. However, the respectively optimum speeds have to be determined in response to the material.

Preferably, the first toothing extends from a tip of the head towards an end of the head at the shaft side. Thus the first toothing extends over the entire length of the head and is used for the main removal work, i.e. for roughing operations.

Depending on the type of the material to be machined and the rotational direction of the tool, the first toothing is straight-toothed, or has a left-hand or right-hand helix or twist (the terms helix and twist shall be regarded as equivalent within the meaning of this invention). In the case of a toothing having a helix, the helix angle is preferably between 4° and 6°. Preferably, the dental tool can also be constructed in symmetry with a plane containing the central axis of the dental tool.

The second toothing is advantageously provided on the cutting edges of the first toothing. For example, the second toothing may be designed as a staggered toothing which comprises cutting edges extending in a direction transverse to the cutting edges of the first toothing. The second toothing can primarily be used for the fine-machining of a surface. Hence, it is preferably used for finishing work. Preferably, the second toothing is arranged at a helix angle of about 25° to 35°.

To improve the cutting capacity as well as the removing capacity, the second toothing advantageously comprises a plurality of cutting edges. Preferably, a plurality of cutting edges of the second toothing are provided on the first toothing. The removing capacity of the dental tool can further be increased thereby. Apart from an active cutting edge, the second toothing also comprises a smoothing cutting edge which is in particular used for finishing work, thereby creating a surface of reduced roughness.

In a preferred embodiment, the third toothing is designed as a transverse cut. In particular, the chip dimensions can thus be influenced in a positive manner such that the size of the separated chips is relatively small. As a result, the chips can be discharged in a simplified manner. Moreover, a transverse cut avoids undesired vibrations of the dental tool during machining.

Preferably, the transverse cut of the third toothing which is provided on the first toothing is differently designed on a cutting edge of the first toothing. As a consequence, the cutting edges of the first toothing are different from those of the third toothing.

Advantageously, the second toothing and the third toothing have opposite helices. Very small cutting segments can thereby be produced on the head of the dental tool, resulting in a diamond-like cutting-edge geometry. Thus the dental tool can inter alia be used in both rotational directions.

In a preferred embodiment, two toothings of the third toothing are respectively provided between two adjacent toothings of the second toothing. As a result, the chip production, in particular, can advantageously be influenced in the form of small chips, and undesired vibrations can also be avoided while the surface is being machined.

To create a toothing which has a cutting effect in both rotational directions of the tool, the third toothing is advantageously identical with the second toothing, with the two toothings having an opposite helix. This results in a diamond toothing having rhombic cutting segments, with a plurality of cutting edges of the two toothings being in respective engagement.

BRIEF DESCRIPTION OF THE DRAWINGS

The present invention shall now be described with reference to embodiments taken in conjunction with the drawing, in which:

FIG. 1a is a lateral view of a first toothing of a dental tool according to a first embodiment of the present invention;

FIG. 1b is an enlarged view showing a detail of the first toothing illustrated in FIG. 1a;

FIG. 2a is a lateral view of the dental tool shown in FIG. 1a and comprising a first and a second toothing;

FIG. 2b is an enlarged view showing a detail of the first and second toothings illustrated in FIG. 2a;

FIG. 3a is a lateral view of a dental tool shown in FIG. 2a and comprising a third toothing;

FIG. 3b is an enlarged view showing a detail of the first, second and third toothings illustrated in FIG. 3a;

FIG. 4b is an enlarged view showing a detail of the first toothing illustrated in FIG. 4a;

FIG. 5b is an enlarged view showing a detail of the first and second toothings illustrated in FIG. 5a.

DETAILED DESCRIPTION

Figure 6:
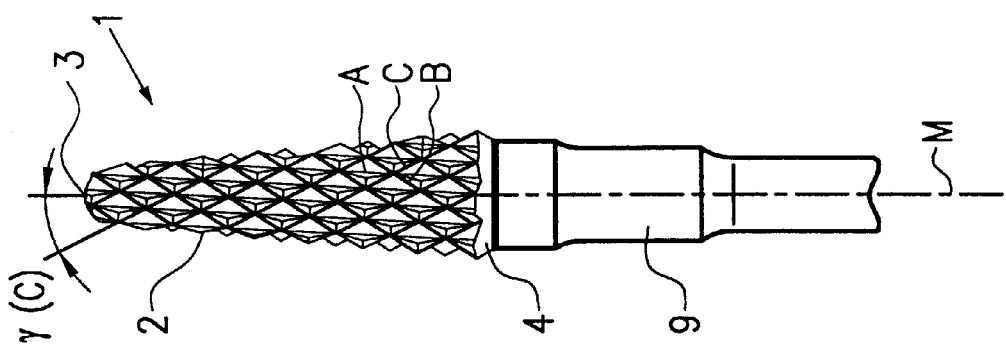
FIG. 6 is a lateral view of the dental tool shown in FIG. 5a and comprising a third toothing.

A first embodiment of a dental tool according to the invention shall now be described with reference to FIGS. 1a to 3b.

A dental tool 1 comprises a head 2 provided with cutting edges, as well as a shaft 9 which can rotatably be supported and driven in a standard tool receiving means.

As shown in FIG. 1a, a first toothing A is provided on head 2. Said first toothing A is designed as a basic toothing which extends from a tip 3 of the head 2 to the end 4 of the head at the shaft side. The cutting edges of the first toothing converge in the tip 3 of the head. As becomes apparent from FIG. 1a and the enlarged detail view 1b, the toothing A has a left-hand helix with a helix angle $\alpha$. However, it is also possible that the first toothing is straight-toothed or has a right-hand helix. Said first toothing A serves as a basic toothing which performs the main cutting work and is mainly used for roughing the material to be machined.

In the present example the helix angle is $\alpha=5°$. However, it may also be chosen to be somewhat greater or smaller, depending on the material to be machined.

As shown in FIGS. 2a and 2b, a second toothing B is is provided on the first toothing A. The second toothing B has a left-hand helix of an angle $\beta$ which is greater than the helix angle $\alpha$ of the first toothing A. In the present embodiment the angle is $\beta=60°$, but can also be chosen to be greater or smaller.

As becomes apparent from the illustration in FIG. 2b, which is drawn on an enlarged scale, toothing B has a groove 7 as well as two cutting edges 5, 6. The cutting edge 5 is here designed as an active cutting edge which, in addition to the main cutting edge of the first toothing A, has a removing or abrading effect, thereby improving the cutting and removing capacity. Furthermore, the second toothing B comprises a smoothing cutting edge 6 which during machining serves to smooth the surface.

FIG. 3a shows the dental tool of the invention with the complete triple toothing. A third toothing C is here additionally provided that is also arranged on the first toothing A. In the upper portion of the head 2a double toothing of the third toothing C is respectively provided between two adjacent cutting edges of the second toothing B. By contrast, in the lower portion of the head 2, only one toothing of the third toothing C is arranged between two adjacent cutting edges of the toothing B (cf. FIG. 3a).

For the sake of clarity, the triple toothing is shown in FIG. 3b on an enlarged scale. The cutting characteristics of the dental tool 1 can be influenced by the third toothing C, which is designed as a transverse cut, in such a manner that no vibrations are observed during machining and the size of the chips is relatively small. Furthermore, the transverse cut C is conducive to the smoothing and roughing characteristics of the dental tool 1. Thus, the dental tool of the invention with the triple toothing permits a final machining of the material without any tool change.

FIGS. 4a to 6 show a second embodiment of the present invention. Like or similar parts have been designated with the same reference numerals as in the first embodiment.

Figure 4B:
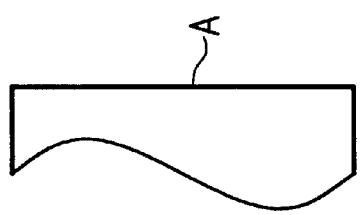
Figure 4A:
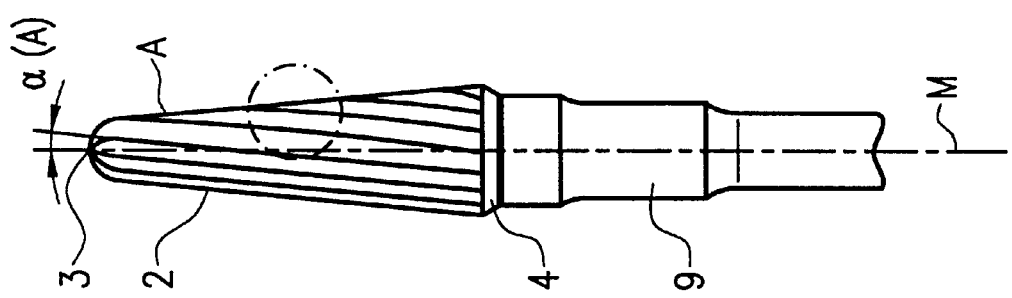
FIG. 4a is a lateral view of a dental tool of the invention according to a second embodiment of the present invention with a first toothing.

As shown in FIG. 4a, the dental tool 1 of the second embodiment is equipped on head 2 with a first toothing A that extends from a tip 3 to an end 4 of the head at the shaft side. The individual cutting edges of the first toothing A converge in the tip 3 of the head. The toothing A has a left-hand helix with an angle $\alpha$ of 5° which, however, can also be chosen such that it is greater or smaller. Head 2 has provided thereon a shaft 9 which can be inserted into a tool receiving means of a drive device. The first toothing A is shown on an enlarged scale in FIG. 4b.

Figure 5B:
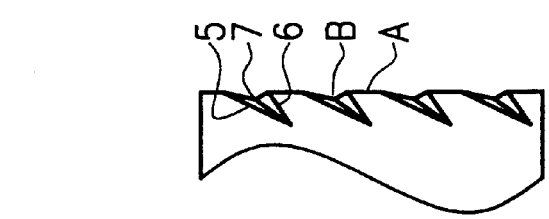
Figure 5A:
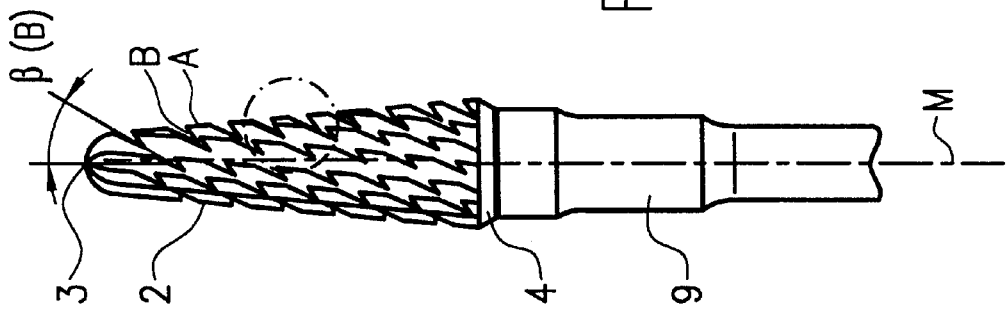
FIG. 5a is a lateral view of the dental tool shown in FIG. 4a and comprising a second toothing.

FIG. 5a shows the dental tool of the second embodiment provided with the second toothing B. As becomes apparent from the enlarged view of FIG. 5b, the second toothing B is mounted on the first toothing A and is also toothed with a left-hand helix. The second toothing B has a helix angle $\beta$ of about 30°. The helix anlge $\beta$ can however also be chosen such that it is greater or smaller.

As shown in FIG. 5b, the second toothing B comprises two cutting edges 5, 6. A groove 7 is arranged between the two cutting edges 5, 6. The cutting edge 5 is an active cutting edge which enhances the cutting performance. The cutting edge 6 is a smoothing cutting edge which primarily has a finishing effect and is used for smoothing the surface to be machined.

FIG. 6 shows the complete dental tool 1 of the second embodiment, which is designed as a universal milling cutter.

As becomes apparent from FIG. 6, the third toothing C has a right-hand helix with a helix angle $\gamma$. Apart from that, however, the third toothing C is identical with the second tothing B, resulting in a tool which has very small cutting segments and a diamond-like cutting-edge geometry. Thus the tool of the second embodiment is suited for anticlockwise and also clockwise use.

In general, it should be noted that the dental technician can additionally influence the cutting characteristics of the inventive dental tool by selecting a corresponding speed. A high speed is in particular used for roughing purposes whereas a low speed serves to finish and produce a smooth surface. However, the respectively optimum speeds must be determined in response to the respective materials.

In summary, the present invention relates to a dental tool 1 comprising a head 2 and a rotatably supportable shaft 9. Head 2 comprises a first toothing A, a second toothing B, and a third toothing C. Hence, different materials can be roughed and also finished by means of said triple toothing.

The present invention is not limited to the illustrated embodiments. Rather, many modifications and alterations are possible within the scope of the present disclosure.

What is claimed is:

1. A dental tool comprising a head (2) and a shaft (9) which can rotatably be supported in a drive device, characterized in that said head (2) comprises a first toothing (A) defined by a first set of generally parallel cutting edges, a second toothing (B) defined by a second set of generally parallel cutting edges inclined with respect to the first set of generally parallel cutting edges, and a third toothing (C) defined by a third set of generally parallel cutting edges inclined with respect to both the first set of generally parallel cutting edges and the second set of generally parallel cutting edges.

2. The dental tool according to claim 1, characterized in that said first toothing (A) extends from a tip (3) of said head (2) to the end (4) of said head (2) at the shaft side.

3. The dental tool according to claim 1 or 2, characterized in that said toothing (A) is straight-toothed.

4. The dental tool according to claim 1 or 2, characterized in that said first toothing (A) is toothed with a left-hand helix.

5. The dental tool according to claim 1 or 2, characterized in that said first toothing (A) is toothed with a right-hand helix.

6. The dental tool according to claim 1 or 2, characterized in that said first toothing (A) has a helix angle (α) between 4° and 6°.

7. The dental tool according to claim 1, characterized in that said second toothing (B) is provided on the cutting edges of said first toothing (A).

8. The dental tool according to claim 7, characterized in that said second toothing (B) is toothed at a helix angle of about 25° to 35°.

9. The dental tool according to claim 1, characterized in that said second toothing comprises a plurality of cutting edges (5, 6).

10. The dental tool according to claim 9, characterized in that said second toothing (B) comprises an active cutting edge (5) and a smoothing cutting edge (6).

11. The dental tool according to claim 9, characterized in that a plurality of cutting edges (5, 6) of said second toothing (B) are provided on said first toothing (A).

12. The dental tool according to claim 1, characterized in that said third toothing (C) is provided on said first toothing (A) and is designed as a transverse cut.

13. The dental tool according to claim 12, characterized in that said transverse cut (C) is differently designed on a cutting edge of said first toothing (A).

14. The dental tool according to claim 1, characterized in that said second toothing (B) and said third toothing (C) have opposite helices.

15. The dental tool according to claim 1, characterized in that said third toothing (C) is identical with said second toothing (B), said third toothing (C) having a helix opposite to said second toothing (B).

* * * * *